US011236352B2

(12) United States Patent
Safro et al.

(10) Patent No.: US 11,236,352 B2
(45) Date of Patent: Feb. 1, 2022

(54) TRANSGENIC PLANTS RESISTANT TO NON-PROTEIN AMINO ACIDS

(71) Applicant: Yeda Research and Development Co. Ltd., Rehovot (IL)

(72) Inventors: Mark Safro, Rehovot (IL); Liron Klipcan, Rehovot (IL); Inbar Maymon, Rehovot (IL); Igal Finarov, Rehovot (IL)

(73) Assignee: YEDA RESEARCH AND DEVELOPMENT CO. LTD., Rehovot (IL)

( * ) Notice: Subject to any disclaimer, the term of this patent is extended or adjusted under 35 U.S.C. 154(b) by 0 days.

(21) Appl. No.: 16/208,640

(22) Filed: Dec. 4, 2018

(65) Prior Publication Data
US 2019/0085350 A1 Mar. 21, 2019

Related U.S. Application Data

(63) Continuation of application No. 14/268,314, filed on May 2, 2014, now abandoned, which is a continuation of application No. PCT/IL2012/050433, filed on Nov. 1, 2012.

(60) Provisional application No. 61/554,993, filed on Nov. 3, 2011.

(51) Int. Cl.
C12N 15/82 (2006.01)
C12N 9/00 (2006.01)

(52) U.S. Cl.
CPC .......... *C12N 15/8251* (2013.01); *C12N 9/93* (2013.01); *C12N 15/821* (2013.01); *C12N 15/8274* (2013.01)

(58) Field of Classification Search
None
See application file for complete search history.

(56) References Cited

U.S. PATENT DOCUMENTS

| 2002/0042097 | A1 | 4/2002 | Tirrell et al. | |
| 2008/0261815 | A1* | 10/2008 | Weston | A01N 37/42 504/322 |
| 2009/0226966 | A1 | 9/2009 | Yokoyama et al. | |
| 2014/0237686 | A1 | 8/2014 | Safro et al. | |

FOREIGN PATENT DOCUMENTS

| WO | WO 00/18963 | 4/2000 |
| WO | WO 2005/077171 | 8/2005 |
| WO | WO 2005/090582 | 9/2005 |
| WO | WO 2006/086474 | 8/2006 |
| WO | WO 2007/103307 | 9/2007 |
| WO | WO 2013/065048 | 5/2013 |

OTHER PUBLICATIONS

Huang et al., 2010, Pleiotropic physiological consequences of feedback-insensitive phenylalanine biosynthesis in *Arabidopsis thaliana*, The Plant Journal 63: 823-835.*
Klipcan et al., 2009, Eukaryotic cytosolic and mitochondrial phenylalanyl-tRNAsynthetases catalyze the charging of tRNA with the meta-tyrosine, Proceedings of the National Academy of Sciences USA 106: 11045-11048.*
Bertin et al., 2008, Grass roots chemistry: meta-Tyrosine, an herbicidal nonprotein amino acid, Proceedings of the National Academy of Sciences USA 104: 16964-16969.*
Tester and Bacic, 2005, Abiotic Stress Tolerance in Grasses. From Model Plant to Crop Plants, Plant Physiology 137: 791-793.*
Chakraborty and Banerjee (Chakraborty and Banerjee, 2016, Phenylalanyl-tRNA synthetase, Research and Reports in Biochemistry 6: 25-38.*
Oburger and Jones, Sampling root exudates—Mission impossible?, Rhizosphere 6: 116-133.*
European Search Report and the European Search Opinion dated Apr. 26, 2017 From the European Patent Office Re. Application No. 16190303.4. (9 Pages).
International Preliminary Report on Patentability dated May 6, 2014 From the International Bureau of WIPO Re. Application No. PCT/IL2012/050433.
International Search Report and the Written Opinion dated Mar. 7, 2013 From the International Searching Authority Re. Application No. PCT/IL2012/050433.
Office Action and Search Report dated May 11, 2015 From the State Intellectual Property Office of the People's Republic of China Re. Application No. 201280053924.7 and Its Translation Into English.
Official Action dated Jun. 5, 2018 From the US Patent and Trademark Office Re. U.S. Appl. No. 14/268,314. (20 pages).
Official Action dated Aug. 17, 2016 From the US Patent and Trademark Office Re. U.S. Appl. No. 14/268,314.
Official Action dated Dec. 22, 2016 From the US Patent and Trademark Office Re. U.S. Appl. No. 14/268,314. (21 pages).
Official Action dated Sep. 27, 2017 From the US Patent and Trademark Office Re. U.S. Appl. No. 14/268,314. (23 pages).
Bertin et al. "Grass Roots Chemistry: Meta-Tyrosine, An Herbicidal Nonprotein Amino Acid", Proc. Natl. Acad. Sci. USA, PNAS, XP002692357, 104(43): 16964-16969, Oct. 23, 2007.
Erikson et al. "The DsdA Gene From *Escherichia coli* Provides A Novel Selectable Marker for Plant Transformation", Plant Molecular Biology, XP019262650, 57(3): 425-433, Feb. 2005.
Fishman et al. "Structure at 2.6. A Resolution of Phenylalanyl-tRNA Synthetase Complexed With Phenylalanyl-Adenylate in the Presence of Manganese", Acta Crystallographica Section D, Biological Crystallography, D57(pt. 11): 1534-1544, 2001.

(Continued)

*Primary Examiner* — Bratislav Stankovic
(74) *Attorney, Agent, or Firm* — Gary J. Gershik

(57) ABSTRACT

Transgenic plants resistant to bio-herbicides, particularly to phytotoxic non-protein amino acids including the meta-tyrosine (m-tyrosine) amino acid analog and salts thereof, means and methods for producing the transgenic plants.

13 Claims, 2 Drawing Sheets

Specification includes a Sequence Listing.

(56) References Cited

OTHER PUBLICATIONS

Huang et al. "Pleiotropic Physiological Consequences of Feedback-Insensitive Phenylalanine Biosynthesis in *Arabidopsis thaliana*", The Plant Journal 63(5): 823-835, Published Online Aug. 3, 2010.
Klipcan et al. "Eukaryotic Cytosolic and Mitochondrial Phenylalanyl-tRNA Synthetases Catalyze the Charging of tRNA With the Meta-Tyrosine", Proc. Natl. Acad. Sci. USA, PNAS, XP002692358, 106(27): 11045-11048, Jul. 7, 2009.
Kotik-Kogan et al. "Structural Basis for Discrimination of L-Phenylalanine From L-Tyrosine by Phenylalanyl-tRNA Synthetase", Structure, 13(12): 1799-1807, Dec. 2005.
Leopold et al. "A Precise Reconstruction of the Emergence and Constrained Radiations of *Escherichia coli* 0157 Portrayed By Backbone Concatenomic Analysis", *Escherichia coli*, Database NCBI [Online], GenBank: EU900200.1, Database Accession No. EU900200, Jun. 8, 2009.
Leopold et al. "A Precise Reconstruction of the Emergence and Constrained Radiations of *Escherichia coli* 0157 Portrayed by Backbone Concatenomic Analysis", *Escherichia coli*, Database NCBI [Online], GenBank: EU900206.1, Database Accession No. EU900206, Jun. 8, 2009.
Ling et al. "Mechanism of tRNA-Dependent Editing in Translational Quality Control", Proc. Natl. Acad. Sci. USA, PNAS, 104(1): 72-77, Jan. 2, 2007.
Potrykus "Gene Transfer to Plants: Assessment of Public Approaches and Results", Annual Review of Plant Physiology & Plant Molecular Biology, 42: 205-225, 1991.
PubChem "DL-m-Tyrosine", Open Chemistry Database, CID 13052 Information, p. 1-24, Jul. 19, 2005.
Roy et al. "Loss of Editing Activity During the Evolution of Mitochondrial Phenylalanyl-tRNA Synthetase", The Journal of Biological Chemistry, 280(46): 205-225, Published Online Sep. 14, 2005.
Shimamoto et al. "Fertile Transgenic Rice Plants Regenerated From Transformed Protoplasts", Nature, 338: 274-276, Mar. 16, 1989.
Tester et al. "Abiotic Stress Tolerance in Grasses. From Model Plants to Crop Plants", Plant Physiology, 137: 791-793, Mar. 2005.
Allen et al., "Expression of 16 Nitrogenase Proteins within the Plant Mitochondria Matrix", (2017) Front Plant Sci. 8, 287.
Goldgur et al., "The crystal structure of Phenylalanyl-tRNA synthetase from Thermus thermophilus complexed with cognate tRNAPhe", (1997) Structure, 5, 59-69.
Mermershtain et al., "Idiosyncrasy and identity in the prokaryotic phe-system: crystal structure of *E. coli* phenylalanine-tRNA synthetase complexed with phenylalanine and AMP", (2011) Protein Science, 20, 160-167.
Evdokimov et al., "Rational protein engineering in action: The first crystal structure of a phenylalanine tRNA synthetase from *Staphylococcus haemolyticus*", (2008) Journal of Structural Biology, 162, 152-169 (abstract only).
Barciszewski et al., "Conservation of the structures of plant tRNAs and aminoacyl-tRNA synthetases", (1979) FEBS Letters 102, 194-197.
Feb. 15, 2017 Decision On Motions 37 C.F.R 41.125(a) in connection with Patent Interference No. 106,048.
Sep. 10, 2020 Decision On Motions 37 C.F.R 41.125(a) in connection with Patent Interference No. 106,115.

* cited by examiner

TRANSGENIC PLANTS RESISTANT TO NON-PROTEIN AMINO ACIDS

RELATED APPLICATIONS

This application is a continuation of U.S. patent application Ser. No. 14/268,314 filed on May 2, 2014, which is a continuation of PCT Patent Application No. PCT/IL2012/050433 having International Filing Date of Nov. 1, 2012, which claims the benefit of priority of U.S. Provisional Patent Application No. 61/554,993 filed on Nov. 3, 2011. The contents of the above applications are all incorporated by reference as if fully set forth herein in their entirety.

SEQUENCE LISTING STATEMENT

The ASCII file, entitled 76043SequenceListing.txt, created on Nov. 28, 2018, comprising 230,993 bytes, submitted concurrently with the filing of this application is incorporated herein by reference.

FIELD OF THE INVENTION

The present invention relates to transgenic plants resistant to bio-herbicides, particularly to phytotoxic non-protein amino acids including meta-tyrosine amino acid analog and salts thereof and to methods for producing the transgenic plants.

BACKGROUND OF THE INVENTION

"Allelopathy" is a term referring to an effect (inhibitory or stimulatory) of a plant on surrounding species by chemicals (allelochemicals) released by the plant into the environment. The allelochemicals are usually secondary metabolites that can be synthesized in any of the plant parts, and can have beneficial (positive allelopathy) or detrimental (negative allelopathy) effects on the target organisms. Allelochemicals are not required for the metabolism (i.e. growth, development and reproduction) of the allelopathic (resistant) plant, but interfere with vital metabolic pathways of non-resistant species providing relative advantage to the resistant plant. The allelopathic effect was realized already in the Greek era. The advantage of allelopathic effect of several widely used crop plants such as wheat, rice and cucumber is known and used. Lately the awareness of the potential to implement this phenomenon in weed management has risen. Among other observed allelochemicals, meta-tyrosine, which shows promising phytotoxic activity, was proposed as possible environmental friendly weed suppressor (Bertin C. et al., 2007. Proceedings of the National Academy of Sciences of U.S.A 104, 16964-16969).

Meta-tyrosine (m-Tyr) is naturally occurring non-protein amino acid. It can be produced by two possible synthesis routes: through the pathway of dopamine synthesis or by oxidation of phenylalanine by reactive oxygen species. The m-Tyr, an isomer of the common protein amino acid tyrosine (p-tyrosine), has been found in *Euphorbia myrsinites* (donkey tail spurge) and some fescue species. Originating from plants, m-Tyr was found to be toxic to a broad spectrum of species. At a concentration as low as 2 μM added to an agar medium m-Tyr inhibits *Arabidopsis thaliana* root growth by 50%, and completely prevents seed germination at a concentration of 50 μM (Bertin C. et al. 2007. ibid).

The appearance of m-tyrosine (m-Tyr) along with o-tyrosine (o-Tyr) and L-dopa within proteins has been widely used as an index for the degree of oxidative damage caused to the proteins. It has been demonstrated that in eukaryotic cells, certain exogenously supplied oxidized amino acids, including m-Tyr, can be incorporated into proteins by the cell biosynthetic pathways rather than via chemical reactions. It is therefore likely that in many cases, amino acids damaged in vivo are available for de-novo synthesis of proteins. This theory is supported by the finding that exposure to m-Tyr results in growth inhibition of a wide range of plant species including commercially important monocot and dicot crop plants. It has been further suggested that the phytotoxicity of m-Tyr is caused by its incorporation into proteins in place of phenylalanine during protein synthesis.

Phenylalanyl-tRNA synthetase (PheRS) belongs to the family of aminoacyl-tRNA synthetases (aaRS), which play critical role in translation of the genetic code. The aaRSs ensure the fidelity of the translation of the genetic code, covalently attaching appropriate amino acids to the corresponding nucleic acid adaptor molecules—tRNA. The aaRSs are a notoriously diverse family of enzymes, varying considerably in primary sequence, subunit size and oligomeric organization. Phylogenetic and structural analyses reveal three major forms of PheRS: a) heterotetrameric (αβ)2 bacterial PheRS; b) heterotetrameric (αβ)2 archaeal/eukaryotic-cytoplasmic PheRS: and c) monomeric mitochondrial PheRS.

The accuracy of aminoacylation reaction promoted by aaRSs, and PheRS in particular, is based on precise recognition of the amino acid substrate. However, due to stereochemical similarity shared by several amino acids, mistakes in recognition occur. Phenylalanine (Phe) and Tyrosine (Tyr) are distinguished by only one hydroxyl group at the aromatic ring and thus differentiation between Phe and Tyr is not always fulfilled. PheRS successfully differentiates between these amino acids with a mistake rate of 1:1000. A higher level of total accuracy of protein biosynthesis is ensured by an editing activity of PheRS along with other aaRSs. The editing activity is associated with the specific site, where misacylated tRNAs are hydrolyzed.

Some of the inventors of the present invention and co-workers investigated the ability of PheRSs from various sources, including bacterial (*Thermus thermophilus* (Tt) and *Escherichia coli* (Ec)) and human (cytosolic (Hsct) and mitochondrial (Hsmt)) source to activate m-Tyr and attach it to tRNA$^{Phe}$ (Klipcan, L., et al., 2009. Proceedings of the National Academy of Sciences U.S.A 106, 11045-11048). The radical-damaged amino acid is activated by these enzymes as assayed by ATP hydrolysis. Steady-state kinetic measurements of aminoacylation (assayed by means of acidic gel electrophoresis) revealed no mischarging of tRNA$^{Phe}$ with m-Tyr by bacterial PheRS (FIG. 1). This observation serves as an indication for the efficiency of the editing mechanism. Moreover, when the bacterial PheRS is incubated with preloaded m-Tyr-tRNA$^{Phe}$, the m-Tyr was deacylated from the tRNA providing the evidence for the so-called trans-editing activity (Ling, J. et al., 2007. Proceedings of the National Academy of Sciences U.S.A 104, 72-77). On the contrary, the mitochondrial enzyme could stably synthesize m-Tyr-tRNA$^{Phe}$. The HsmtPheRS does not contain editing domain and therefore cannot deacylate the non cognate amino acids from tRNA (Roy, H. et al., 2005. The Journal of biological chemistry 280, 38186-38192; Kotik-Kogan, O. et al., 2005. Structure 13, 1799-1807), providing the path for these residues to be incorporated into the protein polypeptide chains. Analysis of kinetic parameters of tRNA$^{Phe}$ aminoacylation shows that the catalytic efficiency ($k_{cat}/K_m$) of m-Tyr attachment by HsmtPheRS is only fivefold lower than that of the correct amino acid, primarily due to a higher $K_m$ value. Relatively high catalytic activity of mitochondrial PheRS toward m-Tyr and lack of editing activity can explain the profound toxic effect of m-Tyr has on plants. In plants, more than 150 proteins are expressed in the mitochondria and chloroplasts, and the monomeric phenylalanyl-tRNA synthetase (PheRS), present in plant organelles is closely resembled to the human mitochondrial PheRS. Thus, incorporation of m-Tyr instead of Phe into organellar proteins results in a large number of damaged proteins, therefore reducing cell viability. The moderate toxicity of m-Tyr to mammalian cells can be explained by the fact that in these cells a mitochondrion encodes only 13 proteins.

Reducing the use of herbicides has become a significant target in keeping sustainable agriculture and landscape management. There is an ongoing effort in developing biological and organic approaches for weed control that can effectively replace the use of hazardous chemicals. At the same time, efforts are made to have means and methods for protecting crop plants from the phytotoxic compounds taking the molecular genetics approach and/or employing natural products.

For example, International PCT Application Publication No. WO/2005/077171 discloses methods for protecting plants from herbicide injury and damage by coating or priming seeds with one or more amino acids to confer tolerance to herbicides that disrupt production of the amino acids by a plant treated with the herbicide.

The significant toxicity of m-Tyr to plants but the reduced effect on fungi, mammals or bacteria has led to its development as a bio-herbicide. U.S. Patent Application Publication No. 20080261815 discloses methods of using m-tyrosine compounds from *Festuca* species for inhibiting weed growth and enhancing growth of non-weed plants, and further discloses methods of identifying plants having herbicidal properties. The shortage of the use of m-Tyrosine as a bioherbicide is that it is toxic not only to weeds but also to crop plants.

There is a recognized need for it would be highly effective to have means for producing transgenic plants, particularly crop or ornamental plants that are resistant to phytotoxic allelochemical, for example to non-protein amino acids including m-Tyrosine.

SUMMARY OF THE INVENTION

The present invention provides means and methods for conferring to transgenic plants resistance to the presence of phytotoxic non-protein amino acids in the plant growth medium. The present invention further provides transgenic plants resistant to phytotoxic non-protein amino acids, particularly to meta-tyrosine (m-Tyr) and salts thereof.

The present invention is based in part on the unexpected discovery that expressing bacterial phenylalanyl-tRNA synthetase (PheRS) within a plant cell, particularly when the PheRS is expressed within the mitochondria and/or chloroplast, confers resistance of the plant to meta-tyrosine. This resistance is due to the ability of the introduced bacterial PheRS to hydrolyze the misacylated m-Tyr-tRNA$^{Phe}$ and to prevent the incorporation of the non-protein amino acid into proteins.

Thus, according to one aspect, the present invention provides a transgenic plant comprising at least one cell comprising at least one exogenous polynucleotide encoding an aminoacyl tRNA synthetase (aaRS) or a fragment thereof, the aaRS or a fragment thereof comprising an editing module capable of hydrolyzing tRNA misacylated with non-protein amino acid analog, wherein the plant is resistant to the non-protein amino acid analog and salts thereof.

In the context of the present invention, the term "resistant to non-protein amino acid analog" refers to the ability of the transgenic plant to grow in a growth medium comprising the non-protein amino acid analog in a concentration that significantly inhibits the growth of a corresponding non-transgenic plant. According to certain embodiments, growth inhibition is shown by at least one of reduced root length, reduced root radical, reduced root mass, reduced plant height, aberrant change in a plant tissue morphology or color, reduced plant shoot mass and/or number and any combination thereof. According to some embodiments, the isolated non-protein amino acid analog or a composition comprising same is added to the growth medium. According to other embodiments, the non-protein amino acid analog is secreted to the growth medium from a plant producing same.

According to certain embodiments, the non-protein amino acid analog is meta-tyrosine (m-Tyr) compound and the aaRS is phenylalanyl-tRNA synthetase (PheRS).

According to certain embodiments, the m-Tyr compound has a formula of Formula I or a salt thereof:

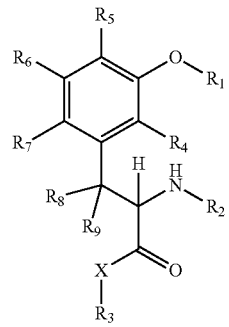

Formula I

Wherein $R_1$ and $R_2$ are independently selected from the group consisting of H, sulfonate, sulfonamide, phosphonate, alkyl, alkenyl, alkynyl, alkoxy, alkoxycarbonyl, saccharide, cycloalkyl, heterocycloalkyl, aryl and heteroaryl, wherein each of the phosphonate, alkyl, alkenyl, alkynyl, alkoxy, alkoxycarbonyl, saccharide, cycloalkyl, heterocycloalkyl, aryl, and heteroaryl is either substituted or unsubstituted;

$R_3$ is selected from the group consisting of H, alkyl, alkenyl, alkynyl, alkoxy, alkoxycarbonyl, saccharide, cycloalkyl, heterocycloalkyl, aryl, and heteroaryl, wherein each of the alkyl, alkenyl, alkynyl, alkoxy, alkoxycarbonyl, saccharide, cycloalkyl, heterocycloalkyl, aryl, and heteroaryl is either substituted or unsubstituted;

X is selected from the group consisting of O and N—Y, wherein Y is selected from the group consisting of H, alkyl, alkenyl, alkynyl, alkoxy, alkoxycarbonyl, saccharide, cycloalkyl, heterocycloalkyl, aryl, and heteroaryl, wherein each of the alkyl, alkenyl, alkynyl, alkoxy, alkoxycarbonyl, saccharide, cycloalkyl, heterocycloalkyl, aryl, and heteroaryl is either substituted or unsubstituted;

$R_4$, $R_5$, $R_6$, and $R_7$ are independently selected from the group consisting of H, hydroxyl, halogen, amino, and nitro; and $R_8$ and $R_9$ are independently selected from the group consisting of H, hydroxyl, halogen, amino, methyl, and halogenated methyl.

According to certain typical embodiments, the m-Tyr compound has the formula of Formula II:

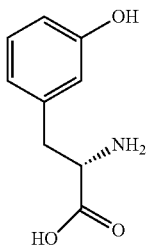 [SMILES: N[C@@H](Cc1cccc(O)c1)C(=O)O]

According to certain currently typical embodiments, the PheRS is bacterial PheRS. Bacterial PheRS is known to be heterotetrameric, comprising two α and two β subunits. According to certain embodiments, the α- and β-subunits are encoded by a single polynucleotide. According to other embodiments, each of the α- and β-subunits is encoded by a separate polynucleotide. According to yet further embodiments, the bacterial PheRS comprises at least one β-subunit or a fragment thereof comprising the editing module.

According to some embodiments, the bacterial PheRS is a heterotetrameric bacterial PheRS selected from the group consisting of Escherichia coli (E. coli) PheRS and Thermus thermophilus PheRS.

According to certain embodiments, the E. Coli PheRS-α subunit is encoded by a polynucleotide having the nucleic acid sequence set forth in SEQ ID NO:1 and the E. Coli PheRS-β subunit is encoded by a polynucleotide having the nucleic acid sequence set forth in SEQ ID NO:2.

According to other embodiments, the E. Coli PheRS-α subunit comprises the amino acid sequence set forth in SEQ ID NO:3 and the E. Coli PheRS-subunit comprises the amino acid sequence set forth in SEQ ID NO:4.

According to other embodiments, the T. thermophilus PheRS-α subunit comprises the amino acid sequence set forth in SEQ ID NO:5 and the T. thermophilus PheRS-β subunit comprises the amino acid sequence set forth in SEQ ID NO:6.

According to certain embodiments, the polynucleotide encoding the aaRS or a fragment thereof comprising the editing module further comprises a nucleic acid sequence encoding a targeting peptide selected from the group consisting of a mitochondrial targeting peptide and a chloroplast targeting peptide. The mitochondrial and chloroplast targeting peptides can be the same or different. Typically, the polynucleotide is so designed that the encoded targeting peptide is fused at the amino terminus (N-terminus) of the encoded aaRS polypeptide.

According to certain embodiments, the transgenic plant comprises a combination of the exogenous polynucleotide encoding the aminoacyl tRNA synthetase (aaRS) or a fragment thereof further comprising the nucleic acid sequence encoding the mitochondrial targeting peptide and the exogenous polynucleotide encoding the aaRS or a fragment thereof further comprising the nucleic acid sequence encoding a chloroplast targeting peptide. The chloroplast targeting peptide and the mitochondrial targeting peptide can be the same or different.

According to certain embodiments, the mitochondrial and the chloroplast targeting peptides are encoded by the nucleic acid sequence set forth in SEQ ID NO:7 and have the amino acid sequence set forth in SEQ ID NO:8.

According to yet other embodiments, the polynucleotides of the present invention are incorporated in a DNA construct enabling their expression in the plant cell. According to one embodiment, the DNA construct comprises at least one expression regulating element selected from the group consisting of a promoter, an enhancer, an origin of replication, a transcription termination sequence, a polyadenylation signal and the like.

According to some embodiments, the DNA construct comprises a promoter. The promoter can be constitutive, induced or tissue specific promoter as is known in the art. Each possibility represents a separate embodiment of the present invention. According to some embodiments, the promoter is a constitutive promoter operable in a plant cell. According to other embodiments, the promoter is root specific promoter. According to further embodiments, the DNA construct further comprises transcription termination and polyadenylation sequence signals.

Optionally, the DNA construct further comprises a nucleic acid sequence encoding a detection marker enabling a convenient selection of the transgenic plant. According to certain currently typical embodiments, the detection marker is selected from the group consisting of a polynucleotide encoding a protein conferring resistance to antibiotic; a polynucleotide encoding a protein conferring resistance to herbicide and a combination thereof.

The present invention also encompasses seeds of the transgenic plant, wherein plants grown from said seeds are resistant to phytotoxic non-protein amino acid analog, particularly to m-Tyr. The present invention further encompasses fruit, leaves or any part of the transgenic plant, as well as tissue cultures derived thereof and plants regenerated therefrom.

According to yet another aspect, the present invention provides a method for producing a transgenic plant resistant to phytotoxic non-protein amino acid analog or a salt thereof, comprising (a) transforming a plant cell with at least one exogenous polynucleotide encoding an aminoacyl tRNA synthetase (aaRS) or a fragment thereof comprising an editing module, the editing module capable of hydrolyzing non-protein aminoacylated tRNA; and (b) regenerating the transformed cell into a transgenic plant resistant to the phytotoxic non-protein amino acid analog or a salt thereof.

The exogenous polynucleotide(s) encoding the aminoacyl tRNA synthetase (aaRS) or a fragment thereof comprising the editing module, capable of hydrolyzing non-protein aminoacylated tRNA according to the teachings of the present invention can be introduced into a DNA construct to include the entire elements necessary for transcription and translation as described above, such that the polypeptides are expressed within the plant cell.

Transformation of plants with a polynucleotide or a DNA construct may be performed by various means, as is known to one skilled in the art. Common methods are exemplified by, but are not restricted to, Agrobacterium-mediated transformation, microprojectile bombardment, pollen mediated transfer, plant RNA virus mediated transformation, liposome mediated transformation, direct gene transfer (e.g. by microinjection) and electroporation of compact embryogenic calli. According to one embodiment, the transgenic plants of the present invention are produced using Agrobacterium mediated transformation.

Transgenic plants comprising the exogenous polynucleotides encoding aaRS or a fragment thereof comprising the editing module according to the teachings of the present invention may be selected employing standard methods of molecular genetics, as are known to a person of ordinary skill in the art. According to certain embodiments, the transgenic plants are selected according to their resistance to an antibiotic or herbicide. According to one embodiment, the antibiotic serving as a selectable marker is one of the group consisting of cefotaxime, vancomycin and kanamycin. According to another embodiment, the herbicide serving as a selectable marker is the non-selective herbicide glufosinate-ammonium (BASTA®).

According to yet other embodiments, the transgenic plants of the invention are selected based on their resistance to the phytotoxic non-protein amino acid analog or salts thereof.

Any plant can be transformed with the polynucleotides of the present invention to produce the transgenic plants resistant to the presence of phytotoxic non-protein amino acid analog, particularly m-Tyr or a salt thereof in the plant growth medium. According to typical embodiments, the plant is a crop plant or an ornamental plant.

Other objects, features and advantages of the present invention will become clear from the following description and drawings.

BRIEF DESCRIPTION OF THE SEVERAL VIEWS OF THE DRAWINGS

FIG. 1A: Aminoacylation of *E. coli* tRNA$^{Phe}$ transcript (1.2 μM) with Phe or m-Tyr by human mitochondrial (Hsmt)PheRS (210 nM) or *Thermus thermophilus* (Tt)PheRS (24 nM) analyzed by electrophoresis in 8% denaturing gel at acidic conditions (0.1 M Na-acetate, pH 5). FIG. 1B: Specific deacylation of m-Tyr-tRNA$^{Phe}$. *E. coli* tRNA$^{Phe}$ transcript (1.2 μM) was aminoacylated with Phe (25 μM), m-Tyr (125 μM) or Tyr (1 mM) by HsmtPheRS (250 nM in experiments with Phe and m-Tyr, or 500 nM in experiments with Tyr) for 5 min; then the reaction was continued after addition (shown by arrows) of TtPheRS (16 nM), *E. coli* (Ec)PheRS (48 nM) or HsctPheRS (32 nM) (retrieved from Klipcan L. et al. 2009, ibid).

DESCRIPTION OF SPECIFIC EMBODIMENTS OF THE INVENTION

Figure 1A:
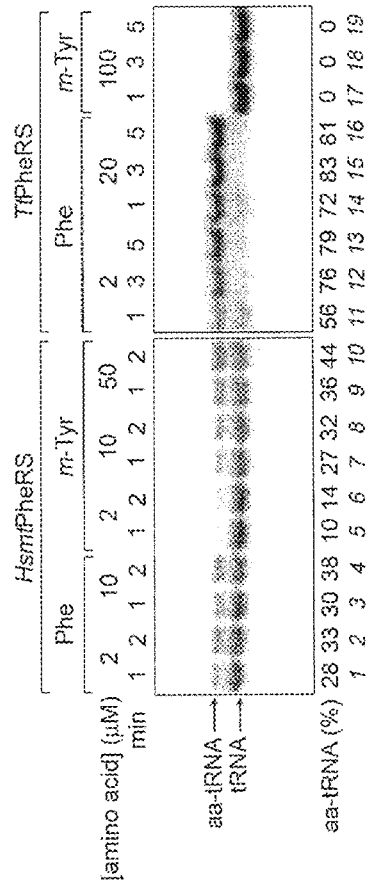
FIGS. 1A-1B show the aminoacylation of tRNA$^{Phe}$ with native and non-protein amino acids and specific deacylation of mischarged product.
Figure 1B:
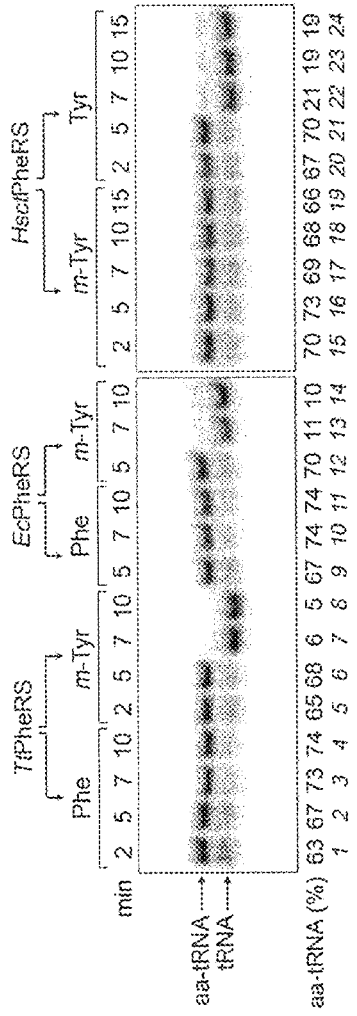

The present invention provides transgenic plants that are resistant to the presence of a phytotoxic non-protein amino acid in the growth medium such that the growth of the resistant plant is essentially not affected by the phytotoxic amino acid. The present invention further provides means and method for producing the transgenic plants of the invention. According to certain embodiments, the phytotoxic non-protein amino acid is a meta-tyrosine (m-Tyr) compound or a salt thereof.

Definitions

The terms "aminoacyl tRNA synthetase" or "aaRS" are used herein as is common in the background art. aaRS is an enzyme that catalyzes the esterification of a specific amino acid or its precursor to one of all its compatible cognate tRNAs to form an aminoacyl-tRNA. The editing module of aaRS has evolved to correct misacylation of non-cognate amino acids to the tRNA, which result in mistranslation of the genetic code. The editing module is capable of hydrolyzing the ester linkage between the non-cognate amino acid and the tRNA. The term "fragment thereof" when used with reference to the aaRS enzyme refers to a fragment of the enzyme which preserves its catalytic activity and further comprises the enzyme editing module that is capable of hydrolyzing a non-protein amino acid miscaylated to the tRNA.

The terms "non-protein amino acid" and ""non-protein amino acid analog" are used herein interchangeably and refer to amino acids not included in the set of the 22 canonical amino acids as is common in the background art.

The term "plant" is used herein in its broadest sense. It includes, but is not limited to, any species of woody, herbaceous, perennial or annual plant. It also refers to a plurality of plant cells that are largely differentiated into a structure that is present at any stage of a plant's development. Such structures include, but are not limited to, a root, stem, shoot, leaf, flower, petal, fruit, etc.

As used herein, the term "growth medium" refers to any medium that can be used to support growth of a plant, and can include, without limitation, various types of soils or plant nutrient media. Suitable examples of soils include, without limitation, natural soil and artificial soil.

The terms "polynucleotide", "polynucleotide sequence", "nucleic acid sequence", and "isolated polynucleotide" are used interchangeably herein. These terms encompass nucleotide sequences and the like. A polynucleotide may be a polymer of RNA or DNA or hybrid thereof, that is single- or double-stranded, linear or branched, and that optionally contains synthetic, non-natural or altered nucleotide bases. The terms also encompass RNA/DNA hybrids.

The term "construct" as used herein refers to an artificially assembled or isolated nucleic acid molecule which includes the gene of interest. In general a construct may include the gene or genes of interest, a marker gene which in some cases can also be the gene of interest and appropriate regulatory sequences. It should be appreciated that the inclusion of regulatory sequences in a construct is optional, for example, such sequences may not be required in situations where the regulatory sequences of a host cell are to be used. The term construct includes vectors but should not be seen as being limited thereto.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation.

The terms "promoter element," "promoter," or "promoter sequence" as used herein, refer to a DNA sequence that is located at the 5' end (i.e. precedes) the protein coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters which cause a gene to be expressed in most cell types at most times are commonly referred to as "constitutive promoters". New promoters of various types useful in plant cells are constantly being discovered; numerous examples may be found in Okamuro J K and Goldberg R B (1989) Biochemistry of Plants 15:1-82.

As used herein, the term an "enhancer" refers to a DNA sequence which can stimulate promoter activity, and may be an innate element of the promoter or a heterologous element inserted to enhance the level or tissue-specificity of a promoter.

The term "expression", as used herein, refers to the production of a functional end-product e.g., an mRNA or a protein.

The term "transgenic" when used in reference to a plant or seed (i.e., a "transgenic plant" or a "transgenic seed") refers to a plant or seed that contains at least one exogenous transcribeable polynucleotide in one or more of its cells. The term "transgenic plant material" refers broadly to a plant, a plant structure, a plant tissue, a plant seed or a plant cell that contains at least one exogenous polynucleotide in at least one of its cells. The exogenous polynucleotide can be a plant endogenous polynucleotide located at a different site or under a different regulation compared to the wild type situation, or a heterologous polynucleotide isolated from a different organism. A "transgenic plant" and a "corresponding non transgenic plant" as used herein refer to a plant comprising at least one cell comprising an exogenous transcribeable polynucleotide and to a plant of the same type lacking said exogenous transcribeable polynucleotide.

The terms "transformants" or "transformed cells" include the primary transformed cell and cultures derived from that cell regardless to the number of transfers. All progeny may not be precisely identical in DNA content, due to deliberate or inadvertent mutations. Mutant progeny that have the same functionality as screened for in the originally transformed cell are included in the definition of transformants.

Transformation of a cell may be stable or transient. The term "transient transformation" or "transiently transformed" refers to the introduction of one or more exogenous polynucleotides into a cell in the absence of integration of the exogenous polynucleotide into the host cell's genome. Transient transformation may be detected by, for example, enzyme-linked immunosorbent assay (ELISA), which detects the presence of a polypeptide encoded by one or more of the exogenous polynucleotides. Alternatively, transient transformation may be detected by detecting the activity of the protein (e.g. -glucuronidase) encoded by the exogenous polynucleotide.

The term "transient transformant" refers to a cell which has transiently incorporated one or more exogenous polynucleotides. In contrast, the term "stable transformation" or "stably transformed" refers to the introduction and integration of one or more exogenous polynucleotides into the genome of a cell. Stable transformation of a cell may be detected by Southern blot hybridization of genomic DNA of the cell with nucleic acid sequences which are capable of binding to one or more of the exogenous polynucleotides. Alternatively, stable transformation of a cell may also be detected by enzyme activity of an integrated gene in growing tissue or by the polymerase chain reaction of genomic DNA of the cell to amplify exogenous polynucleotide sequences. The term "stable transformant" refers to a cell which has stably integrated one or more exogenous polynucleotides into the genomic or organellar DNA. It is to be understood that a plant or a plant cell transformed with the nucleic acids, constructs and/or vectors of the present invention can be transiently as well as stably transformed. The terms "polypeptide," "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

Among thousands known non-protein amino acids, about 300 are found in plants. Many of them are structurally similar to those considered as regular amino-acid substrates of aminoacyl tRNA synthetases (aaRSs). Amino acid side-chain modifications may be generated in vivo by reactive oxygen species (ROS) such as hydroxyl radicals and superoxide anions. Very often the modifications are associated with production of one or more hydroxyl group in para-, meta- or ortho-positions on the aromatic ring of phenylalanine and tyrosine. However, the pathways of ROS-damaged amino acids incorporation into polypeptide chains remained unclear, taking into account editing activity of aaRSs.

The present invention now shows that (i) mitochondrial and cytoplasmic phenylalanyl-tRNA synthetases (defined HsmtPheRS and HsctPheRS, respectively) catalyze direct attachment of m-Tyr to tRNA$^{Phe}$, thereby opening the way for delivery of the misacylated tRNA to the ribosome and incorporation of m-Tyr into eukaryotic proteins; and (ii) the presence of bacterial PheRS in mitochondria and/or chloroplast induces plant resistance to m-Tyr. These finding form the basis for developing systems of non-protein amino acids herbicides and plants resistant to these herbicides.

According to one aspect, the present invention provides a transgenic plant comprising at least one cell comprising at least one exogenous polynucleotide encoding an aminoacyl tRNA synthetase (aaRS) or a fragment thereof, the aaRS or a fragment thereof comprising an editing module capable of hydrolyzing tRNA misacylated with non-protein amino acid analog, wherein the plant is resistant to the non-protein amino acid analog and salts thereof.

The teachings of the present invention are exemplified by the production of transgenic plants expressing a bacterial phenylalanyl-tRNA synthetase (PheRS), that are resistant to the phytotoxic effect of m-Tyr compounds and salts thereof. However, it is to be explicitly understood that the scope of the present invention encompasses any combination of a phytotoxic non-protein amino acid and aminoacyl tRNA synthetase (aaRS) or a fragment thereof, as long as the aaRS or its fragment comprises an editing module capable of hydrolyzing the non-protein amino acid from the tRNA.

The aaRS can be a native enzyme having an efficient editing activity as exemplified herein for *E. coli* PheRS. Alternatively, the aaRS can be genetically modified as to induce or increase the editing activity. The significant plasticity of the synthetic and editing sites of aaRSs, particularly PheRS and minor changes in their stereo-chemical organization, can be used for designing the architecture of these sites to change the binding affinity towards the small ligands or to control hydrolytic activity towards misacylated tRNAs (Kotik-Kogan, O., Moor et al., 2005. Structure 13, 1799-

1807; Fishman, R. et al. 2001. Acta crystallographica 57, 1534-1544). The exogenous aaRS, which is preferably located within the mitochondrion and chloroplast cellular organelles can repair the mistakes incorporated into proteins by the wild type aaRS enzymes using the extra-editing activity, and/or chelate the harmful amino acid analog and prevent its incorporation into the proteins.

Cloning of a polynucleotide encoding the aaRS can be performed by any method as is known to a person skilled in the art. Various DNA constructs may be used to express the aaRS in a desired plant.

The present invention provides a DNA construct or an expression vector comprising a polynucleotide encoding aaRS, which may further comprise regulatory elements, including, but not limited to, a promoter, an enhancer, and a termination signal.

Among the most commonly used promoters are the nopaline synthase (NOS) promoter (Ebert et al., 1987 Proc. Natl. Acad. Sci. U.S.A. 84:5745-5749), the octapine synthase (OCS) promoter, caulimovirus promoters such as the cauliflower mosaic virus (CaMV) 19S promoter (Lawton et al., 1987 Plant Mol Biol. 9:315-324), the CaMV 35S promoter (Odell et al., 1985 Nature 313:810-812), and the figwort mosaic virus 35S promoter, the light inducible promoter from the small subunit of rubisco, the Adh promoter (Walker et al., 1987 Proc Natl Aca. Sci U.S.A. 84:6624-66280, the sucrose synthase promoter (Yang et al., 1990 Proc. Natl. Acad. Sci. U.S.A. 87:4144-4148), the R gene complex promoter (Chandler et al., 1989. Plant Cell 1:1175-1183), the chlorophyll a/b binding protein gene promoter, etc. Other commonly used promoters are the promoters for the potato tuber ADPGPP genes, the sucrose synthase promoter, the granule bound starch synthase promoter, the glutelin gene promoter, the maize waxy promoter, Brittle gene promoter, and Shrunken 2 promoter, the acid chitinase gene promoter, and the zein gene promoters (15 kD, 16 kD, 19 kD, 22 kD, and 27 kD; Perdersen et al. 1982 Cell 29:1015-1026). A plethora of promoters is described in International Patent Application Publication No. WO 00/18963. According to certain currently typical embodiments, the construct of the present invention comprises the constitutive CaMV 35S promoter.

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht I L et al. (1989. Plant Cell 1:671-680).

In particular embodiments of the present invention, four clones of E. coli PheRS subunits: EcPheRSα, mtp-EcPheRSα, EcPheRSβ, and mtp-EcPheRSβ were prepared under the regulation of the constitutive promoter 35S and carried resistance to the non-selective herbicide glufosinate-ammonium (BASTA®) (EcPheRSα and mtp-EcPheRSα) or kanamycin (EcPheRSβ, and mtp-EcPheRSβ). The mtp-EcPheRSα and mtp-EcPheRSβ further included dual (mitochondrial and chloroplast) targeting peptide. The clones were transformed into Arabidopsis thaliana plants (Columbia (Col-0) ecotype) via Agrobacterium tumefaciens.

Those skilled in the art will appreciate that the various components of the nucleic acid sequences and the transformation vectors described in the present invention are operatively linked, so as to result in expression of said nucleic acid or nucleic acid fragment Techniques for operatively linking the components of the constructs and vectors of the present invention are well known to those skilled in the art. Such techniques include the use of linkers, such as synthetic linkers, for example including one or more restriction enzyme sites.

According to yet another aspect, the present invention provides a method for producing a transgenic plant resistant to phytotoxic non-protein amino acid analog or a salt thereof, comprising (a) transforming a plant cell with at least one exogenous polynucleotide encoding an aminoacyl tRNA synthetase (aaRS) or a fragment thereof comprising an editing module capable of hydrolyzing tRNA aminoacylated with non-protein amino acid; and (b) regenerating the transformed cell into a transgenic plant resistant to the phytotoxic non-protein amino acid analog or a salt thereof.

Methods for transforming a plant cell with nucleic acids sequences according to the present invention are known in the art. As used herein the term "transformation" or "transforming" describes a process by which a foreign DNA, such as a DNA construct, enters and changes a recipient cell into a transformed, genetically modified or transgenic cell. Transformation may be stable, wherein the nucleic acid sequence is integrated into the plant genome and as such represents a stable and inherited trait, or transient, wherein the nucleic acid sequence is expressed by the cell transformed but is not integrated into the genome, and as such represents a transient trait. According to typical embodiments the nucleic acid sequence of the present invention is stably transformed into a plant cell.

There are various methods of introducing foreign genes into both monocotyledonous and dicotyledonous plants (for example, Potrykus I. 1991. Annu Rev Plant Physiol Plant Mol Biol 42:205-225; Shimamoto K. et al., 1989. Nature 338:274-276).

The principal methods of the stable integration of exogenous DNA into plant genomic DNA includes two main approaches:

Agrobacterium-mediated gene transfer: The Agrobacterium-mediated system includes the use of plasmid vectors that contain defined DNA segments which integrate into the plant genomic DNA. Methods of inoculation of the plant tissue vary depending upon the plant species and the Agrobacterium delivery system. A widely used approach is the leaf-disc procedure, which can be performed with any tissue explant that provides a good source for initiation of whole-plant differentiation (Horsch et al., 1988. Plant Molecular Biology Manual A5, 1-9, Kluwer Academic Publishers, Dordrecht). A supplementary approach employs the Agrobacterium delivery system in combination with vacuum infiltration. The Agrobacterium system is especially useful in the generation of transgenic dicotyledenous plants.

Direct DNA uptake: There are various methods of direct DNA transfer into plant cells. In electroporation, the protoplasts are briefly exposed to a strong electric field, opening up mini-pores to allow DNA to enter. In microinjection, the DNA is mechanically injected directly into the cells using micropipettes. In microparticle bombardment, the DNA is adsorbed on microprojectiles such as magnesium sulfate crystals or tungsten particles, and the microprojectiles are physically accelerated into cells or plant tissues.

According to certain embodiments, transformation of the DNA constructs of the present invention into a plant cell is performed using Agrobacterium system.

The transgenic plant is then grown under conditions suitable for the expression of the recombinant DNA construct or constructs. Expression of the recombinant DNA construct or constructs reduce the plant susceptibility to non-protein amino acid analogs, particularly to m-tyrosine.

The regeneration, development and cultivation of plants from single plant protoplast transformants or from various transformed explants is well known in the art (Weissbach and Weissbach, In: Methods for Plant Molecular Biology, (Eds.), 1988 Academic Press, Inc., San Diego, Calif.). This regeneration and growth process typically includes the steps of selection of transformed cells, culturing those individualized cells or tissues through the usual stages of embryonic development through the rooted plantlet stage. Transgenic embryos and seeds are similarly regenerated. The resulting transgenic rooted shoots are thereafter planted in an appropriate plant growth medium such as soil.

Selection of transgenic plants transformed with a nucleic acid sequence of the present invention as to provide transgenic plants comprising the exogenous aaRS is performed employing standard methods of molecular genetics, known to a person of ordinary skill in the art. According to certain embodiments, the nucleic acid sequence further comprises a nucleic acid sequence encoding a product conferring resistance to antibiotic, and thus transgenic plants are selected according to their resistance to the antibiotic. According to some embodiments, the antibiotic serving as a selectable marker is one of the aminoglycoside group consisting of paromomycin and kanamycin. According to additional embodiments, the nucleic acid sequence further comprises a nucleic acid sequence encoding a product conferring resistance to an herbicide, including, but not limited to, resistant to the non-selective herbicide glufosinate-ammonium (BASTA®). Methods for detecting the presence and/or expression of the exogenous polynucleotide within the transgenic plants are also known to a person skilled in the art, and include, for example, PCR, Northern and Southern hybridization. As exemplified herein, the final confirmation for obtaining a transgenic plant of the present invention is obtained by growing the transgenic plants comprising the exogenous polynucleotide in a medium comprising phytotoxic concentration of the non-protein amino acid. Only plants expressing an active aaRS or a fragment thereof having the editing module can normally grow under these conditions.

Also within the scope of this invention are seeds or plant parts obtained from the transgenic plants that maintain the resistance to phytotoxic concentration of the non-protein amino acid. Plant parts include differentiated and undifferentiated tissues, including but not limited to, roots, stems, shoots, leaves, pollen, seeds, tumor tissue, and various forms of cells and culture such as single cells, protoplasts, embryos, and callus tissue. The plant tissue may be in the plant or in organ, tissue or cell culture.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Material and Methods

Four clones of *E. coli* PheRS subunits: EcPheRSα, mtp-EcPheRSα, EcPheRSβ, and mtp-EcPheRSβ were prepared under the regulation of the constitutive promoter 35S and carried resistance to BASTA (EcPheRSα and mtp-EcPheRSα) or kanamycin (EcPheRSβ, and mtp-EcPheRSβ). The mtp-EcPheRSα and mtp-EcPheRSβ contained dual (mitochondrial and chloroplast) targeting peptide. The clones were transformed into *Arabidopsis thaliana* plants (Columbia (Col-0) ecotype) via *Agrobacterium tumefaciens*.

For transformation, plants were grown in a growth room under controlled conditions (temperature 22° C., 8 hours light) for 30 days and then transformed as described hereinbelow. Wild type and transformed seeds were sterilized, cold-treated, and germinated on sterile MS media with or without antibiotic. After germination the plants were planted in pots and transferred to the growth room (22° C. 16 hours light).

*Agrobacterium* Infiltration Transformation

*Agrobacterium tumefaciens* strain ABI harboring the binary vectors pART27 or pMLBart was used for transformation. Both vectors contain the nptII gene as a selectable marker. Small scale *Agrobacterium* cultures were grown in liquid LB medium with appropriate antibiotics at 28° C. overnight. The small scale cultures were then diluted 50-fold into LB medium with appropriate antibiotics for large scale overnight cultures. Cells were then harvested by centrifugation at 5000 r.p.m. (about 3000 g) for 15 min, and re-suspended in infiltration medium to an OD600 of 0.8.

Inoculations were performed by dipping aerial parts of the plants for 30 second in 300 ml of a solution containing 5% (w/v) Sucrose, 10 mM $MgCl_2$, re-suspended *Agrobacterium* cells from a 200-ml overnight culture, and 0.05% of the surfactant (Silwet L-77). After the inoculation plants were left in a low-light or dark location and covered with a transparent plastic dome to maintain humidity; the dome was removed and the plants returned to the growth chamber 12 to 24 h after inoculation. Transformed plants were kept in the greenhouse and seeds were harvested upon full maturation.

Plant Selection

The seeds were germinated on soil and transgenic plants were selected by spraying with 0.1% BASTA® herbicide in the greenhouse. Spraying was performed one week after germination and repeated four times at two-day intervals. Transgenic plants were readily identified at the end of the BASTA® selection. While such plants continued to grow and remained green, the untransformed plants remained small, became white and died two weeks after selection. For selection positive plant containing kanamycin resistance, seeds were screened in MS medium supplemented with 50 mg/ml kanamycin.

Crosses

After homozygote plant for each (α- or β-) subunits of PheRS were obtained, they were subjected to crosses. The plants used as females were hand emasculated. Anthers from freshly opened flowers of donor plants were harvested and pollination was performed by touching the anthers onto the stigmas of the emasculated plants. The pollinated flowers were labeled and any remaining opened or unopened flowers from the same plant were removed to avoid any confusion at harvest. The selection of positive plants containing both subunits of PheRS was done as described in the "Plant Selection" section hereinabove.

The m-Tyr Resistance

To assess effects of m-Tyr on *Arabidopsis* root growth, 20 m of m-Try was added to MS medium. *Arabidopsis* seeds were sterilized by shaking in 30% bleach. 0.3% Triton X-100 for 10 min, followed by three rinses with sterile distilled water. Petri dishes with seeds on agar medium were cold-stratified for 72 h at 4° C., and were subsequently placed vertically in green-house at 23° C., under 16:8 h light/dark cycle. After 7 days of growth, the root length of the plant was analyzed.

Figure 2:
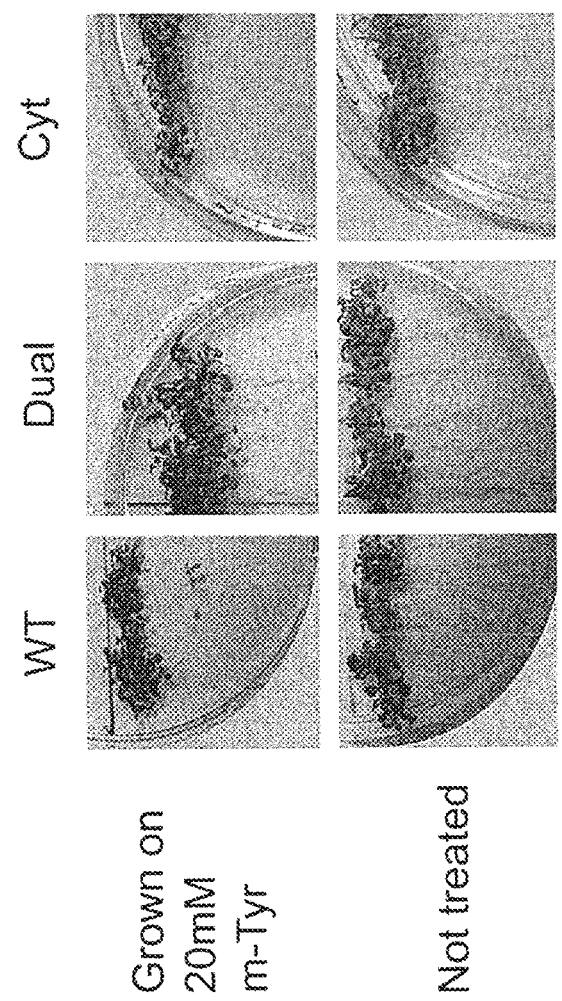
FIG. 2 shows the phenotypes of wild type and transgenic lines of *A. Taliana*. Root growth of Wt (wild type), Cyt (transgenic plant containing cytosol localized bacterial PheRS) and Dual (transgenic plant containing plastids localized bacterial PheRS). Upper panels: samples grown on media containing 20 μM m-Tyrosine. Bottom panels: non-treated samples.

Example 1: The Effect of Bacterial PheRS Expression on *Arabidopsis* Resistance to m-Tyr The bacterial PheRS genes described in the "Material and Methods" section hereinabove were expressed under the control of the constitutive 35S CaMV promoter. A transit peptide was appended to N-terminus of EcPheRS-α and EcPheRS-β subunits of the bacterial enzyme in order to direct them into the mitochondria and chloroplast of *Arabidopsis thaliana*. The second constructs pair including PheRS-α and PheRS-β lacked the transit peptides. Thus, four different constructs were transformed into *Arabidopsis thaliana*, and homozygote self-pollinated plants were generated as described hereinabove. Each line was further crossed to create plants containing heterodimeric EcPheRS possessing editing activity localized in cytoplasm (cyt-PheRS) and heterodimeric EcPheRS localized in plant mitochondria and chloroplast (mtp-PheRS). Several independent transgenic lines were obtained, and their resistance to m-Tyr was analyzed. Resistance to m-Tyr was examined by growing wild-type, cyt-PheRS and mtp-PheRS *Arabidopsis thaliana* lines in Petri dishes containing 20 M m-Tyr in the growth media. Same lines grown on untreated media served as a control. The resistance to m-Tyr was already observed at the F2 generation. Resistance was found to be much more profound for line containing mtp-PheRS (FIG. 2). It can be seen that while the roots of wild type plants didn't develop at 20 M m-Tyr the roots of lines containing mtp-PheRS developed up to the half of the length of the non-treated plants. The roots of cyt-PheRS expressing line are less developed compared to the line containing mtp-PheRS. It is to be noted that the growth of the transgenic *Arabidopsis* plants grown under normal conditions was unaffected considerably by the presence of bacterial PheRS in the cytoplasm or organelles (FIG. 2).

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

What is claimed is:

1. A transgenic plant comprising at least one cell, said at least one cell comprising at least one exogenous polynucleotide encoding a bacterial heterotetrameric phenylalanyl-tRNA synthetase (PheRS), the PheRS comprising an editing module which hydrolyzes phenylalanine tRNA misacylated with a meta-tyrosine (m-Tyr) compound, wherein the plant is resistant to the meta-tyrosine (m-Tyr) compound and salts thereof, wherein said PheRS is targeted to, or expressed in the mitochondria and/or chloroplasts of the transgenic plant, wherein said plant is a dicot, wherein the transgenic plant is resistant to a meta-tyrosine (m-Tyr) compound and salts thereof, and wherein said meta-tyrosine (m-Tyr) compound has the formula of Formula II having the following formula:

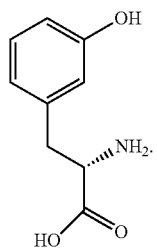 [SMILES: N[C@@H](Cc1cccc(O)c1)C(=O)O]

2. The transgenic plant of claim 1, wherein said plant grows in a medium containing the meta-tyrosine (m-Tyr) compound or salt thereof in a concentration that significantly inhibits the growth of a corresponding non-transgenic plant.

3. The transgenic plant of claim 2, wherein growth inhibition is shown by at least one of reduced root length, reduced root radical, reduced root mass, reduced plant height, aberrant change in a plant tissue morphology or color, reduced plant shoot mass, reduced plant shoot number and any combination thereof.

4. The transgenic plant of claim 1, wherein the heterotetrameric PheRS is a heterotetrameric bacterial PheRS composed of two PheRS-alpha subunits and two PheRS-beta subunits.

5. The transgenic plant of claim 4, wherein the bacterial PheRS is selected from the group consisting of *Escherichia coli* (*E. coli*) PheRS and *Thermus thermophilus* PheRS.

6. The transgenic plant of claim 5, wherein the *E. coli* PheRS-alpha is encoded by a polynucleotide having the nucleic acid sequence set forth in SEQ ID NO: 1 and the *E. coli* PheRS-beta is encoded by a polynucleotide having the nucleic acid sequence set forth in SEQ ID NO: 2.

7. The transgenic plant of claim 5, wherein the *E. coli* PheRS-alpha subunit comprises the amino acid sequence set forth in SEQ ID NO: 3;the *E. coli* PheRS-beta subunit comprises the amino acid sequence set forth in SEQ ID NO: 4; the *T. thermophilus* PheRS-alpha subunit comprises the amino acid sequence set forth in SEQ ID NO: 5; and the *T. thermophilus* PheRS-beta subunit comprises the amino acid sequence set forth in SEQ ID NO:6.

8. The transgenic plant of claim 1, wherein the polynucleotide encoding the heterotetrameric PheRS further comprises a nucleic acid sequence encoding a targeting peptide selected from the group consisting of a mitochondrial targeting peptide and a chloroplast targeting peptide.

9. The transgenic plant of claim 8, wherein said plant comprises a combination of (a) the polynucleotide encoding the PheRS further comprising the nucleic acid sequence encoding a mitochondrial targeting peptide and (b) the polynucleotide encoding the PheRS further comprising the nucleic acid sequence encoding a chloroplast targeting peptide.

10. A seed of the transgenic plant of claim 1, comprising at least one exogenous polynucleotide encoding a heterotetrameric phenylalanyl-tRNA synthetase (PheRS), the PheRS comprising an editing module which hydrolyzes phenylalanyl tRNA misacylated with a meta-tyrosine (m-Tyr) compound, wherein said PheRS is targeted to, or expressed in the mitochondria and/or chloroplasts of the transgenic plant, wherein the transgenic plant is resistant to the meta-tyrosine (m-Tyr) compound and salts thereof, and wherein said meta-tyrosine (m-Tyr) compound has the following formula:

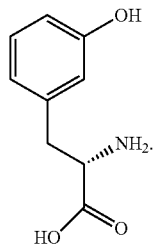 [SMILES: N[C@@H](Cc1cccc(O)c1)C(=O)O]

11. A tissue culture comprising at least one transgenic cell of the plant of claim 1 or a protoplast derived therefrom, wherein the tissue culture regenerates a transgenic plant comprising at least one exogenous polynucleotide encoding a heterotetrameric phenylalanyl-tRNA synthetase (PheRS), the PheRS comprising an editing module which hydrolyzes phenylalanine tRNA misacylated with a meta-tyrosine (m-Tyr) compound, wherein said PheRS is targeted to, or expressed in the mitochondria and/or chloroplasts of the transgenic plant, wherein the transgenic plant is resistant to the meta-tyrosine (m-Tyr) compound and salts thereof, and wherein said meta-tyrosine (m-Tyr) compound has the following formula:

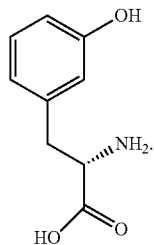 [SMILES: N[C@@H](Cc1cccc(O)c1)C(=O)O]

12. The transgenic plant of claim 1, wherein the heterotetrameric phenylalanyl-tRNA synthetase (PheRS) has the active domains of the *Escherichia coli* (*E. coli*) PheRS.

13. The transgenic plant of claim 1, wherein the heterotetrameric phenylalanyl-tRNA synthetase (PheRS) is the *E. coli* PheRS.

* * * * *

SEQUENCE LISTING

```
<160> NUMBER OF SEQ ID NOS: 8

<210> SEQ ID NO 1
<211> LENGTH: 984
<212> TYPE: DNA
<213> ORGANISM: Escherichia coli
<220> FEATURE:
<221> NAME/KEY: misc_feature
<223> OTHER INFORMATION: E. Coli PheRS subunit alpha

<400> SEQUENCE: 1
atgtcacatc tcgcagaact ggttgccagt gcgaaggcgg ccattagcca ggcgtcagat      60
gttgccgcgt tagacaatgt gcgcgtcgaa tatttgggta aaaagggca cttaacccctt    120 cagatgacga ccctgcgtga gctgccgcca gaagagcgtc cggcagccgg tgcggttatc    180
aacgaagcga aagagcaggt tcagcaggcg ctgaatgcgc gtaaagcgga actggaaagc    240
gctgcactga atgcgcgtct ggcggcggaa acgattgatg tctctctgcc aggtcgtcgc    300
attgaaaacg gcggtctgca tccggttacc cgtaccatcg accgtatcga aagtttcttc    360
ggtgagcttg gctttaccgt ggcaaccggg ccggaaatcg aagacgatta tcataacttc    420
gatgctctga acattcctgg tcaccacccg gcgcgcgctg accacgacac tttctggttt    480
gacgctaccc gcctgctgcg tacccagacc tctggcgtac agatccgcac catgaaagcc    540
cagcagccac cgattcgtat catcgcgcct ggccgtgttt atcgtaacga ctacgaccag    600
actcacacgc cgatgttcca tcagatggaa ggtctgattg ttgataccaa catcagcttt    660
accaacctga aaggcacgct gcacgacttc ctgcgtaact tctttgagga agatttgcag    720
attcgcttcc gtccttccta cttcccgttt accgaacctt ctgcagaagt ggatgtcatg    780
ggtaaaaacg gtaaatggct ggaagtactg ggctgcggga tggtgcatcc gaacgtgctg    840
cgtaacgttg gcatcgaccc ggaagtttac tctggtttcg ccttcgggat ggggatggag    900
cgtctgacta tgttgcgtta cggcgtcacc gacctgcgtt cattcttcga aaacgatctg    960
```

```
cgtttcctca aacagtttaa ataa                                         984
```

<210> SEQ ID NO 2
<211> LENGTH: 2388
<212> TYPE: DNA
<213> ORGANISM: Escherichia coli
<220> FEATURE:
<221> NAME/KEY: misc_feature
<223> OTHER INFORMATION: E. Coli PheRS subunit beta

<400> SEQUENCE: 2

```
atgaaattca gtgaactgtg gttacgcgaa tgggtgaacc cggcgattga tagcgatgcg    60
ctggcgaatc aaatcactat ggcgggcctg gaagttgacg gtgtagaacc ggttgccggt   120
agcttccacg gcgtggtcgt tggtgaagtg gttgagtgtg cgcagcatcc gaacgctgac   180
aaactgcgtg tgacaaaagt gaatgtcggc ggcgatcgcc tgctggacat cgtctgcggt   240
gcgccaaact gccgtcaggg cctgcgtgtg cggtagcga ccattggtgc tgttctgccg    300
ggtgatttca aaattaaagc ggcgaaactg cgcggcgaac cgtctgaagg gatgctgtgc   360
tccttttctg agctgggaat ttctgacgac cataacggca ttatcgaact gcctgcagat   420
gcgccgattg cgactgacat ccgcgaatac ctgaaactcg atgacaacac catcgaaatc   480
agcgtaacgc caaaccgtgc cgactgtttta ggtatcattg gtgttgcgcg tgacgttgcc   540
gtgctgaatc agctgccgct ggttgaaccg gaaatcgttc cggttggtgc gaccatcgac   600
gacacgctgc cgattacagt cgaagcgccg gaagcctgcc cgcgttatct tggccgtgtg   660
gtaaaaggca ttaacgttaa agcgccaact ccgctgtgga tgaaagaaaa actgcgtcgt   720
tgcgggatcc gttctatcga tgcagttgtt gacgtcacca actatgtgct gctcgaattg   780
ggccagccga tgcacgcttt cgataaagat cgcattgaag cggcattgt ggtgcggatg    840
gcgaaagagg gcgaaacgct ggtgctgctc gacggtactg aagcgaagct gaatgctgac   900
actctggtca tcgccgacca caacaaggcg ctggcgatgg cggcatctt cggtggcgaa    960
cactctggcg tgaatgacga acacaaaac gtgctgctgg aatgcgcttt ctttagcccg   1020
ctgtctatca ccggtcgtgc tcgtcgtcat ggcctgcata ctgatgcgtc tcaccgttat   1080
gagcgtggcg ttgatccggc actgcagtac aaagcgatgg aacgtgcgac ccgtctgctg   1140
attgacatct gcggtggtga ggctggtccg gtaattgata tcaccaacga agcaacgctg   1200
ccgaagcgtg caaccatcac tttacgtcgt agcaaactgg atcgcctgat cggccatcat   1260
attgcggatg agcaggtaac tgacattctg cgtcgtctcg gctgcgaagt gaccgaaggc   1320
aaagacgagt ggcaggcagt gcgccgagc tggcgtttcg acatggagat tgaagaagat   1380
ctggtcgaag aagtcgcgcg tgtttacggc tacaacaaca tcccggatga gccggtacag   1440
gcaagcctga ttatgggtac tcaccgtgaa gctgacctgt cgctcaagcg cgtgaaaacg   1500
ctgctcaacg ataaaggcta tcaggaagtg atcacctata gcttcgttga tccgaaagtg   1560
cagcagatga tccatccagg cgttgaagcc ttactgctgc caagcccgat ctctgttgaa   1620
atgtcagcaa tgcgtctttc tctgtggacc ggcctgctgg caaccgtggt gtacaaccag   1680
aaccgtcagc agaaccgtgt gcgcattttc gaaagcggtc tgcgtttcgt accagatact   1740
caggcaccgt tgggcattcg tcaggatctg atgttagccg gtgtgatttg cggtaaccgt   1800
tacgaagagc actggaacct ggcaaaagag accgttgatt tctatgattt gaaaggcgat   1860
cttgaatccg ttctcgacct gaccggtaaa ctgaatgagg ttgagttccg tgcagaagcg   1920
aatccggcac tgcatccggg gcaatccgca gcgatttatc tgaaaggtga acgtattggt   1980
```

```
tttgttgggg ttgttcatcc tgaactggaa cgtaaactgg atcttaacgg tcgcactctg    2040
gtgttcgaac tggagtggaa caagctcgca gaccgcgtgg tgcctcaggc gcgcgagatt    2100
tctcgcttcc cggcgaaccg tcgtgacatc gcggtggtgg tcgcagaaaa cgttcccgca    2160
gcggatattt tatccgaatg taagaaagtt ggcgtaaatc aggtagttgg cgtaaactta    2220
tttgacgtgt accgcggtaa gggtgttgcg gagggtata agagcctcgc cataagcctg    2280
atcctgcaag ataccagccg tacactcgaa gaagaggaga ttgccgctac cgtcgccaaa    2340
tgtgtagagg cattaaaaga gcgattccag gcatcattga gggattga                 2388
```

<210> SEQ ID NO 3
<211> LENGTH: 327
<212> TYPE: PRT
<213> ORGANISM: Escherichia coli
<220> FEATURE:
<221> NAME/KEY: MISC_FEATURE
<223> OTHER INFORMATION: E. Coli PheRS subunit alpha

<400> SEQUENCE: 3

```
Met Ser His Leu Ala Glu Leu Val Ala Ser Ala Lys Ala Ala Ile Ser
1               5                   10                  15

Gln Ala Ser Asp Val Ala Ala Leu Asp Asn Val Arg Val Glu Tyr Leu
            20                  25                  30

Gly Lys Lys Gly His Leu Thr Leu Gln Met Thr Thr Leu Arg Glu Leu
        35                  40                  45

Pro Pro Glu Glu Arg Pro Ala Ala Gly Ala Val Ile Asn Glu Ala Lys
    50                  55                  60

Glu Gln Val Gln Gln Ala Leu Asn Ala Arg Lys Ala Glu Leu Glu Ser
65                  70                  75                  80

Ala Ala Leu Asn Ala Arg Leu Ala Ala Glu Thr Ile Asp Val Ser Leu
                85                  90                  95

Pro Gly Arg Arg Ile Glu Asn Gly Gly Leu His Pro Val Thr Arg Thr
            100                 105                 110

Ile Asp Arg Ile Glu Ser Phe Phe Gly Glu Leu Gly Phe Thr Val Ala
        115                 120                 125

Thr Gly Pro Glu Ile Glu Asp Asp Tyr His Asn Phe Asp Ala Leu Asn
    130                 135                 140

Ile Pro Gly His His Pro Ala Arg Ala Asp His Asp Thr Phe Trp Phe
145                 150                 155                 160

Asp Thr Thr Arg Leu Leu Arg Thr Gln Thr Ser Gly Val Gln Ile Arg
                165                 170                 175

Thr Met Lys Ala Gln Gln Pro Pro Ile Arg Ile Ile Ala Pro Gly Arg
            180                 185                 190

Val Tyr Arg Asn Asp Tyr Asp Gln Thr His Thr Pro Met Phe His Gln
        195                 200                 205

Met Glu Gly Leu Ile Val Asp Thr Asn Ile Ser Phe Thr Asn Leu Lys
    210                 215                 220

Gly Thr Leu His Asp Phe Leu Arg Asn Phe Phe Glu Glu Asp Leu Gln
225                 230                 235                 240

Ile Arg Phe Arg Pro Ser Tyr Phe Pro Phe Thr Glu Pro Ser Ala Glu
                245                 250                 255

Val Asp Val Met Gly Lys Asn Gly Lys Trp Leu Glu Val Leu Gly Cys
            260                 265                 270

Gly Met Val His Pro Asn Val Leu Arg Asn Val Gly Ile Asp Pro Glu
        275                 280                 285
```

```
Val Tyr Ser Gly Phe Ala Phe Met Gly Met Glu Arg Leu Thr Met
    290                 295                 300

Leu Arg Tyr Gly Val Thr Asp Leu Arg Ser Phe Glu Asn Asp Leu
305                 310                 315                 320

Arg Phe Leu Lys Gln Phe Lys
                325

<210> SEQ ID NO 4
<211> LENGTH: 795
<212> TYPE: PRT
<213> ORGANISM: Escherichia coli
<220> FEATURE:
<221> NAME/KEY: MISC_FEATURE
<223> OTHER INFORMATION: E. Coli PheRS subunit beta

<400> SEQUENCE: 4

Met Lys Phe Ser Glu Leu Trp Leu Arg Glu Trp Val Asn Pro Ala Ile
1               5                   10                  15

Asp Ser Asp Ala Leu Ala Asn Gln Ile Thr Met Ala Gly Leu Glu Val
            20                  25                  30

Asp Gly Val Glu Pro Val Ala Gly Ser Phe His Gly Val Val Val Gly
        35                  40                  45

Glu Val Val Glu Cys Ala Gln His Pro Asn Ala Asp Lys Leu Arg Val
    50                  55                  60

Thr Lys Val Asn Val Gly Gly Asp Arg Leu Leu Asp Ile Val Cys Gly
65                  70                  75                  80

Ala Pro Asn Cys Arg Gln Gly Leu Arg Val Ala Val Ala Thr Ile Gly
                85                  90                  95

Ala Val Leu Pro Gly Asp Phe Lys Ile Lys Ala Ala Lys Leu Arg Gly
            100                 105                 110

Glu Pro Ser Glu Gly Met Leu Cys Ser Phe Ser Glu Leu Gly Ile Ser
        115                 120                 125

Asp Asp His Ser Gly Ile Ile Glu Leu Pro Ala Asp Ala Pro Ile Gly
    130                 135                 140

Thr Asp Ile Arg Glu Tyr Leu Lys Leu Asp Asp Asn Thr Ile Glu Ile
145                 150                 155                 160

Ser Val Thr Pro Asn Arg Ala Asp Cys Leu Gly Ile Ile Gly Val Ala
                165                 170                 175

Arg Asp Val Ala Val Leu Asn Gln Leu Pro Leu Val Gln Pro Glu Ile
            180                 185                 190

Val Pro Val Gly Ala Thr Ile Asp Asp Thr Leu Pro Ile Thr Val Glu
        195                 200                 205

Ala Pro Glu Ala Cys Pro Arg Tyr Leu Gly Arg Val Val Lys Gly Ile
    210                 215                 220

Asn Val Lys Ala Pro Thr Pro Leu Trp Met Lys Glu Lys Leu Arg Arg
225                 230                 235                 240

Cys Gly Ile Arg Ser Ile Asp Ala Val Val Asp Val Thr Asn Tyr Val
                245                 250                 255

Leu Leu Glu Leu Gly Gln Pro Met His Ala Phe Asp Lys Asp Arg Ile
            260                 265                 270

Glu Gly Gly Ile Val Val Arg Met Ala Lys Glu Gly Thr Leu Val
        275                 280                 285

Leu Leu Asp Gly Thr Glu Ala Lys Leu Asn Ala Asp Thr Leu Val Ile
    290                 295                 300

Ala Asp His Asn Lys Ala Leu Ala Met Gly Gly Ile Phe Gly Gly Glu
```

```
                305                 310                 315                 320
            His Ser Gly Val Asn Asp Glu Thr Gln Asn Val Leu Leu Glu Cys Ala
                            325                 330                 335

Phe Phe Ser Pro Leu Ser Ile Thr Gly Arg Ala Arg His Gly Leu
                            340                 345                 350

His Thr Asp Ala Ser His Arg Tyr Glu Arg Gly Val Asp Pro Ala Leu
                            355                 360                 365

Gln His Lys Ala Met Glu Arg Ala Thr Arg Leu Leu Ile Asp Ile Cys
                            370                 375                 380

Gly Gly Glu Ala Gly Pro Val Ile Asp Ile Thr Asn Glu Ala Thr Leu
            385                 390                 395                 400

Pro Lys Arg Ala Thr Ile Thr Leu Arg Arg Ser Lys Leu Asp Arg Leu
                            405                 410                 415

Ile Gly His His Ile Ala Asp Glu Gln Val Thr Asp Ile Leu Arg Arg
                            420                 425                 430

Leu Gly Cys Glu Val Thr Glu Gly Lys Asp Glu Trp Gln Ala Val Ala
                            435                 440                 445

Pro Ser Trp Arg Phe Asp Met Glu Ile Glu Glu Asp Leu Val Glu Glu
                            450                 455                 460

Val Ala Arg Val Tyr Gly Tyr Asn Asn Ile Pro Asp Glu Pro Val Gln
            465                 470                 475                 480

Ala Ser Leu Ile Met Gly Thr His Arg Glu Ala Asp Leu Ser Leu Lys
                            485                 490                 495

Arg Val Lys Thr Leu Leu Asn Asp Lys Gly Tyr Gln Glu Val Ile Thr
                            500                 505                 510

Tyr Ser Phe Val Asp Pro Lys Val Gln Gln Met Ile His Pro Gly Val
                            515                 520                 525

Glu Ala Leu Leu Leu Pro Ser Pro Ile Ser Val Glu Met Ser Ala Met
                            530                 535                 540

Arg Leu Ser Leu Trp Thr Gly Leu Leu Ala Thr Val Val Tyr Asn Gln
            545                 550                 555                 560

Asn Arg Gln Gln Asn Arg Val Arg Ile Phe Glu Ser Gly Leu Arg Phe
                            565                 570                 575

Val Pro Asp Thr Gln Ala Pro Leu Gly Ile Arg Gln Asp Leu Met Leu
                            580                 585                 590

Ala Gly Val Ile Cys Gly Asn Arg Tyr Glu Glu His Trp Asn Leu Ala
                            595                 600                 605

Lys Glu Thr Val Asp Phe Tyr Asp Leu Lys Gly Asp Leu Glu Ser Val
                            610                 615                 620

Leu Asp Leu Thr Gly Lys Leu Asn Glu Val Glu Phe Arg Ala Glu Ala
            625                 630                 635                 640

Asn Pro Ala Leu His Pro Gly Gln Ser Ala Ala Ile Tyr Leu Lys Gly
                            645                 650                 655

Glu Arg Ile Gly Phe Val Gly Val Val His Pro Glu Leu Glu Arg Lys
                            660                 665                 670

Leu Asp Leu Asn Gly Arg Thr Leu Val Phe Glu Leu Glu Trp Asn Lys
                            675                 680                 685

Leu Ala Asp Arg Val Val Pro Gln Ala Arg Glu Ile Ser Arg Phe Pro
                            690                 695                 700

Ala Asn Arg Arg Asp Ile Ala Val Val Ala Glu Asn Val Pro Ala
            705                 710                 715                 720

Ala Asp Ile Leu Ser Glu Cys Lys Lys Val Gly Val Asn Gln Val Val
                            725                 730                 735
```

```
Gly Val Asn Leu Phe Asp Val Tyr Arg Gly Lys Gly Val Ala Glu Gly
            740                 745                 750

Tyr Lys Ser Leu Ala Ile Ser Leu Ile Leu Gln Asp Thr Ser Arg Thr
            755                 760                 765

Leu Glu Glu Glu Ile Ala Ala Thr Val Ala Lys Cys Val Glu Ala
            770                 775                 780

Leu Lys Glu Arg Phe Gln Ala Ser Leu Arg Asp
785                 790                 795

<210> SEQ ID NO 5
<211> LENGTH: 350
<212> TYPE: PRT
<213> ORGANISM: Thermus thermophilus
<220> FEATURE:
<221> NAME/KEY: MISC_FEATURE
<223> OTHER INFORMATION: T. thermophilus PheRS subunit alpha

<400> SEQUENCE: 5

Met Leu Glu Glu Ala Leu Ala Ala Ile Gln Asn Ala Arg Asp Leu Glu
1               5                   10                  15

Glu Leu Lys Ala Leu Lys Ala Arg Tyr Leu Gly Lys Lys Gly Leu Leu
            20                  25                  30

Thr Gln Glu Met Lys Gly Leu Ser Ala Leu Pro Leu Glu Glu Arg Arg
        35                  40                  45

Lys Arg Gly Gln Glu Leu Asn Ala Ile Lys Ala Ala Leu Glu Ala Ala
50                  55                  60

Leu Glu Ala Arg Glu Lys Ala Leu Glu Glu Ala Ala Leu Lys Glu Ala
65                  70                  75                  80

Leu Glu Arg Glu Arg Val Asp Val Ser Leu Pro Gly Ala Ser Leu Phe
            85                  90                  95

Ser Gly Gly Leu His Pro Ile Thr Leu Met Glu Arg Glu Leu Val Glu
            100                 105                 110

Ile Phe Arg Ala Leu Gly Tyr Gln Ala Val Gly Pro Glu Val Glu
            115                 120                 125

Ser Glu Phe Phe Asn Phe Asp Ala Leu Asn Ile Pro Glu His His Pro
        130                 135                 140

Ala Arg Asp Met Trp Asp Thr Phe Trp Leu Thr Gly Glu Gly Phe Arg
145                 150                 155                 160

Leu Glu Gly Pro Leu Gly Glu Glu Val Glu Gly Arg Leu Leu Leu Arg
            165                 170                 175

Thr His Thr Ser Pro Met Gln Val Arg Tyr Met Val Ala His Thr Pro
        180                 185                 190

Pro Phe Arg Ile Val Val Pro Gly Arg Val Phe Arg Phe Glu Gln Thr
        195                 200                 205

Asp Ala Thr His Glu Ala Val Phe His Gln Leu Glu Gly Leu Val Val
        210                 215                 220

Gly Glu Gly Ile Ala Met Ala His Leu Lys Gly Ala Ile Tyr Glu Leu
225                 230                 235                 240

Ala Gln Ala Leu Phe Gly Pro Asp Ser Lys Val Arg Phe Gln Pro Val
            245                 250                 255

Tyr Phe Pro Phe Val Glu Pro Gly Ala Gln Phe Ala Val Trp Trp Pro
            260                 265                 270

Glu Gly Gly Lys Trp Leu Glu Leu Gly Gly Ala Gly Met Val His Pro
            275                 280                 285

Lys Val Phe Gln Ala Val Asp Ala Tyr Arg Glu Arg Leu Gly Leu Pro
```

```
            290                 295                 300
Pro Ala Tyr Arg Gly Val Thr Gly Phe Ala Phe Gly Leu Gly Val Glu
305                 310                 315                 320

Arg Leu Ala Met Leu Arg Tyr Gly Ile Pro Asp Ile Arg Tyr Phe Phe
                325                 330                 335

Gly Gly Arg Leu Lys Phe Leu Glu Gln Phe Lys Gly Val Leu
            340                 345                 350

<210> SEQ ID NO 6
<211> LENGTH: 785
<212> TYPE: PRT
<213> ORGANISM: Thermus thermophilus
<220> FEATURE:
<221> NAME/KEY: MISC_FEATURE
<223> OTHER INFORMATION: T. thermophilus PheRS subunit beta

<400> SEQUENCE: 6

Met Arg Val Pro Phe Ser Trp Leu Lys Ala Tyr Val Pro Glu Leu Glu
1               5                   10                  15

Ser Pro Glu Val Leu Glu Arg Leu Ala Gly Leu Gly Phe Glu Thr
            20                  25                  30

Asp Arg Ile Glu Arg Val Phe Pro Ile Pro Arg Gly Val Val Phe Ala
        35                  40                  45

Arg Val Leu Glu Ala His Pro Ile Pro Gly Thr Arg Leu Lys Arg Leu
    50                  55                  60

Val Leu Asp Ala Gly Arg Thr Val Glu Val Val Ser Gly Ala Glu Asn
65                  70                  75                  80

Ala Arg Lys Gly Ile Gly Val Ala Leu Ala Leu Pro Gly Thr Glu Leu
                85                  90                  95

Pro Gly Leu Gly Gln Lys Val Gly Glu Arg Val Ile Gln Gly Val Arg
            100                 105                 110

Ser Phe Gly Met Ala Leu Ser Pro Arg Glu Leu Gly Val Gly Glu Tyr
        115                 120                 125

Gly Gly Gly Leu Leu Glu Phe Pro Glu Asp Ala Leu Pro Pro Gly Thr
130                 135                 140

Pro Leu Ser Glu Ala Trp Pro Glu Glu Val Val Leu Asp Leu Glu Val
145                 150                 155                 160

Thr Pro Asn Arg Pro Asp Ala Leu Gly Leu Leu Gly Leu Ala Arg Asp
                165                 170                 175

Leu His Ala Leu Gly Tyr Ala Leu Val Glu Pro Glu Ala Ala Leu Lys
            180                 185                 190

Ala Glu Ala Leu Pro Leu Pro Phe Ala Leu Lys Val Glu Asp Pro Glu
        195                 200                 205

Gly Ala Pro His Phe Thr Leu Gly Tyr Ala Phe Gly Leu Arg Val Ala
    210                 215                 220

Pro Ser Pro Leu Trp Met Gln Arg Ala Leu Phe Ala Ala Gly Met Arg
225                 230                 235                 240

Pro Ile Asn Asn Val Val Asp Val Thr Asn Tyr Val Met Leu Glu Arg
                245                 250                 255

Ala Gln Pro Met His Ala Phe Asp Leu Arg Phe Val Gly Glu Gly Ile
            260                 265                 270

Ala Val Arg Arg Ala Arg Glu Gly Glu Arg Leu Lys Thr Leu Asp Gly
        275                 280                 285

Val Glu Arg Thr Leu His Pro Glu Asp Leu Val Ile Ala Gly Trp Arg
    290                 295                 300
```

```
Gly Glu Glu Ser Phe Pro Leu Gly Leu Ala Gly Val Met Gly Gly Ala
305                 310                 315                 320

Glu Ser Glu Val Arg Glu Asp Thr Glu Ala Ile Ala Leu Glu Val Ala
            325                 330                 335

Cys Phe Asp Pro Val Ser Ile Arg Lys Thr Ala Arg Arg His Gly Leu
        340                 345                 350

Arg Thr Glu Ala Ser His Arg Phe Glu Arg Gly Val Asp Pro Leu Gly
            355                 360                 365

Gln Val Pro Ala Gln Arg Ala Leu Ser Leu Leu Gln Ala Leu Ala
        370                 375                 380

Gly Ala Arg Val Ala Glu Ala Leu Leu Glu Ala Gly Ser Pro Lys Pro
385                 390                 395                 400

Pro Glu Ala Ile Pro Phe Arg Pro Glu Tyr Ala Asn Arg Leu Leu Gly
                405                 410                 415

Thr Ser Tyr Pro Glu Ala Glu Gln Ile Ala Ile Leu Lys Arg Leu Gly
            420                 425                 430

Cys Arg Val Glu Gly Glu Gly Pro Thr Tyr Arg Val Thr Pro Pro Ser
            435                 440                 445

His Arg Leu Asp Leu Arg Leu Glu Glu Asp Leu Val Glu Glu Val Ala
        450                 455                 460

Arg Ile Gln Gly Tyr Glu Thr Ile Pro Leu Ala Leu Pro Ala Phe Phe
465                 470                 475                 480

Pro Ala Pro Asp Asn Arg Gly Val Glu Ala Pro Tyr Arg Lys Glu Gln
                485                 490                 495

Arg Leu Arg Glu Val Leu Ser Gly Leu Gly Phe Gln Glu Val Tyr Thr
            500                 505                 510

Tyr Ser Phe Met Asp Pro Glu Asp Ala Arg Arg Phe Arg Leu Asp Pro
        515                 520                 525

Pro Arg Leu Leu Leu Leu Asn Pro Leu Ala Pro Glu Lys Ala Ala Leu
530                 535                 540

Arg Thr His Leu Phe Pro Gly Leu Val Arg Val Leu Lys Glu Asn Leu
545                 550                 555                 560

Asp Leu Asp Arg Pro Glu Arg Ala Leu Leu Phe Glu Val Gly Arg Val
                565                 570                 575

Phe Arg Glu Arg Glu Glu Thr His Leu Ala Gly Leu Leu Phe Gly Glu
            580                 585                 590

Gly Val Gly Leu Pro Trp Ala Lys Glu Arg Leu Ser Gly Tyr Phe Leu
        595                 600                 605

Leu Lys Gly Tyr Leu Glu Ala Leu Phe Ala Arg Leu Gly Leu Ala Phe
        610                 615                 620

Arg Val Glu Ala Gln Ala Phe Pro Phe Leu His Pro Gly Val Ser Gly
625                 630                 635                 640

Arg Val Leu Val Glu Gly Glu Val Gly Phe Leu Gly Ala Leu His
            645                 650                 655

Pro Glu Ile Ala Gln Glu Leu Glu Leu Pro Val His Leu Phe Glu
                660                 665                 670

Leu Arg Leu Pro Leu Pro Asp Lys Pro Leu Ala Phe Gln Asp Pro Ser
            675                 680                 685
```

```
Arg His Pro Ala Ala Phe Arg Asp Leu Ala Val Val Pro Ala Pro
    690             695             700
Thr Pro Tyr Gly Glu Val Glu Ala Leu Val Arg Glu Ala Ala Gly Pro
705             710             715             720
Tyr Leu Glu Ser Leu Ala Leu Phe Asp Leu Tyr Gln Gly Pro Pro Leu
            725             730             735
Pro Glu Gly His Lys Ser Leu Ala Phe His Leu Arg Phe Arg His Pro
            740             745             750
Lys Arg Thr Leu Arg Asp Glu Glu Val Glu Glu Ala Val Ser Arg Val
            755             760             765
Ala Glu Ala Leu Arg Ala Arg Gly Phe Gly Leu Arg Gly Leu Asp Thr
    770             775             780
Pro
785

<210> SEQ ID NO 7
<211> LENGTH: 123
<212> TYPE: DNA
<213> ORGANISM: Artificial Sequence
<220> FEATURE:
<223> OTHER INFORMATION: Synthetic polynucleotide

<400> SEQUENCE: 7
ggaatttcta caatggtggg ctcagctctc aggagaggtg cccatgcata tgtctacctg      60
gtgagtaagg ccagtcacat ctccagaggc catcagcacc aggcctgggg atcgaggcct     120
cct                                                                   123

<210> SEQ ID NO 8
<211> LENGTH: 37
<212> TYPE: PRT
<213> ORGANISM: Artificial Sequence
<220> FEATURE:
<223> OTHER INFORMATION: Synthetic Peptide

<400> SEQUENCE: 8

Met Val Gly Ser Ala Leu Arg Arg Gly Ala His Ala Tyr Val Tyr Leu
1               5                   10                  15
Val Ser Lys Ala Ser His Ile Ser Arg Gly His Gln His Gln Ala Trp
            20                  25                  30
Gly Ser Arg Pro Pro
        35
```